United States Patent
Prevost et al.

(10) Patent No.: US 11,242,302 B2
(45) Date of Patent: *Feb. 8, 2022

(54) METHOD FOR PRODUCING PARAXYLENE USING A SIMULATED MOVING-BED STEP, AND A STEP OF FRACTIONATING TWO FRACTIONS IN A TWO-SECTION COLUMN

(71) Applicant: AXENS, Rueil Malmaison (FR)

(72) Inventors: Isabelle Prevost, Rueil Malmaison (FR); Jerome Pigourier, Rueil Malmaison (FR); Gerard Hotier, Rueil Malmaison (FR)

(73) Assignee: AXENS, Rueil Malmaison (FR)

(*) Notice: Subject to any disclaimer, the term of this patent is extended or adjusted under 35 U.S.C. 154(b) by 0 days.

This patent is subject to a terminal disclaimer.

(21) Appl. No.: 17/256,290

(22) PCT Filed: Jun. 21, 2019

(86) PCT No.: PCT/EP2019/066445
§ 371 (c)(1),
(2) Date: Dec. 28, 2020

(87) PCT Pub. No.: WO2020/002142
PCT Pub. Date: Jan. 2, 2020

(65) Prior Publication Data
US 2021/0261483 A1    Aug. 26, 2021

(30) Foreign Application Priority Data

Jun. 29, 2018 (FR) ...................................... 1856049

(51) Int. Cl.
*C07C 7/04* (2006.01)
*C07C 7/13* (2006.01)
(Continued)

(52) U.S. Cl.
CPC .............. *C07C 7/005* (2013.01); *B01D 3/143* (2013.01); *B01D 3/32* (2013.01); *B01D 15/185* (2013.01);
(Continued)

(58) Field of Classification Search
None
See application file for complete search history.

(56) References Cited

U.S. PATENT DOCUMENTS 3,700,744 A * 10/1972 Berger .................... C07C 15/08
585/478
5,284,992 A *  2/1994 Hotier .................... C07C 7/005
585/805
(Continued)

FOREIGN PATENT DOCUMENTS

FR    2844790 A1    3/2004
FR    2862638 A1    5/2005
(Continued)

OTHER PUBLICATIONS

International Search Report PCT/EP2019/066445 dated Sep. 18, 2019 (pp. 1-3).

*Primary Examiner* — Tam M Nguyen
(74) *Attorney, Agent, or Firm* — Millen White Zelano and Branigan, PC; John Sopp

(57) ABSTRACT

The present invention describes a process for obtaining para-xylene from a feedstock containing xylenes, ethylbenzene and C9+ hydrocarbons, said process comprising a single stage A of separation in a simulated moving bed carried out with a zeolite as adsorbent and a desorbent and making it possible to obtain at least three fractions, a fraction A1 comprising a mixture of para-xylene and of desorbent and two fractions A21, A22 comprising ethylbenzene (EB), ortho-xylene (OX) and meta-xylene (MX) and desorbent, said stage is carried out at a
(Continued)

temperature between 20° C. and 250° C., under a pressure between the bubble pressure of the xylenes at the operating temperature and 2.0 MPa, and with a ratio by volume of the desorbent to the feedstock in the unit for separation 2 in a simulated moving bed is between 0.4 and 2.5, a stage B of fractionation by distillation in a 2-cut distillation column of the fractions A21 and A22 resulting from stage A, in which said fractions are introduced separately at distinct injection points, and makes it possible to obtain a fraction B2 containing ethylbenzene, ortho-xylene and meta-xylene, and a fraction B42 devoid of aromatic compounds having 8 carbon atoms and containing desorbent.

17 Claims, 2 Drawing Sheets

(51) Int. Cl.
| | |
|---|---|
| *C07C 7/00* | (2006.01) |
| *B01D 3/14* | (2006.01) |
| *B01D 3/32* | (2006.01) |
| *B01D 15/18* | (2006.01) |
| *C07C 5/27* | (2006.01) |

(52) U.S. Cl.
CPC .......... *B01D 15/1828* (2013.01); *C07C 5/277* (2013.01); *C07C 7/04* (2013.01); *C07C 7/13* (2013.01)

(56) References Cited

U.S. PATENT DOCUMENTS

| | | | |
|---|---|---|---|
| 6,407,303 | B1 | 6/2002 | Dennis |
| 7,592,499 | B2 | 9/2009 | Wolff et al. |
| 7,915,471 | B2 | 3/2011 | Leflaive et al. |
| 8,557,028 | B2 * | 10/2013 | Hurst ................... B01J 20/3042 95/147 |
| 8,802,914 | B2 | 8/2014 | Corradi |
| 9,227,891 | B2 | 1/2016 | Leflaive et al. |
| 10,093,598 | B2 | 10/2018 | Ou et al. |
| 10,954,176 | B2 * | 3/2021 | Prevost ..................... C07C 7/04 |
| 2002/0068844 | A1 * | 6/2002 | Williams ................... C07C 7/13 585/470 |
| 2002/0077519 | A1 * | 6/2002 | Miller ..................... C07C 15/08 585/828 |
| 2002/0099251 | A1 * | 7/2002 | Doyle ..................... C07C 15/08 585/828 |
| 2016/0009614 | A1 * | 1/2016 | Laroche ................. B01J 20/183 585/828 |
| 2018/0009729 | A1 * | 1/2018 | Ou ............................ C07C 7/13 |

FOREIGN PATENT DOCUMENTS

| | | |
|---|---|---|
| FR | 2922547 A1 | 4/2009 |
| WO | 13089902 A1 | 6/2013 |
| WO | 16133589 A1 | 8/2016 |

* cited by examiner

METHOD FOR PRODUCING PARAXYLENE USING A SIMULATED MOVING-BED STEP, AND A STEP OF FRACTIONATING TWO FRACTIONS IN A TWO-SECTION COLUMN

TECHNICAL FIELD para-Xylene is mainly used for the production of terephthalic acid and of polyethylene terephthalate resins, for providing synthetic textiles, bottles, and more generally plastics.

The present invention relates to a process for obtaining high-purity para-xylene employing a specific sequence of stages making it possible to simplify the fractionation stage.

PRIOR ART

The production of high-purity para-xylene employing a stage of separation by adsorption is well known in the prior art. Industrially, said stage is carried out within a "C8-aromatic loop" or "xylene loop" sequence of processes. This "C8-aromatic loop" includes a stage of removal of the heavy compounds (that is to say compounds containing more than 9 carbon atoms, denoted C9+) in a distillation column known as a "xylenes column".

The top stream from this column, which contains the C8-aromatic isomers, is subsequently sent to the process for the separation of the para-xylene, which is generally a stage of separation by adsorption in a simulated moving bed.

The extract obtained on conclusion of the stage of separation by adsorption in a simulated moving bed, which contains the para-xylene, is subsequently distilled by means of an extraction column and then of a toluene column, in order to obtain high-purity para-xylene.

The raffinate obtained on conclusion of the stage of separation by adsorption in a simulated moving bed, which is rich in meta-xylene, ortho-xylene and ethylbenzene, after a stage of removal of the desorbent by distillation, the mixture is employed in an isomerization stage, making it possible to obtain a mixture in which the proportion of xylenes (ortho-, meta- and para-xylenes) is virtually at thermodynamic equilibrium, and the amount of ethylbenzene decreased. This mixture is again sent to the "xylenes column" with the fresh feedstock.

The prior art provides numerous variants of this base scheme employing one or more separation stages (by adsorption, crystallization, distillation or by membrane) and/or one or more gas-phase isomerization stages (converting the ethylbenzene by isomerization into xylenes or by dealkylation into benzene) or liquid-phase isomerization stages (not converting the ethylbenzene).

Patent FR 2 862 638 describes a process for the production of para-xylene from a hydrocarbon feedstock, using two simulated moving bed separation stages and two isomerization stages. The disadvantage of this process is that of requiring two simulated moving bed separation stages, which results in a substantial increase in the production cost.

The main disadvantage of these variants is that of making the process more complex by employing one or more adsorption or isomerization stages. This complexity consequently increases the investment costs for the implementation of said processes.

In the field of the invention, a person skilled in the art is constantly seeking to limit the energy consumption of the aromatic complex while retaining the amount of high-purity para-xylene obtained. This is because the energy impact is assuming growing importance for operators, given the increasing incentives to reduce the carbon footprint of their units.

Surprisingly, the applicant company has discovered that the combination, in a process for obtaining high-purity para-xylene, of a stage of separation by adsorption in a SMB producing two fractions containing a mixture of ethylbenzene (EB), meta-xylene (MX), ortho-xylene (OX) and desorbent in different proportions, said fractions being involved separately in a single column for separation by distillation, advantageously makes it possible to facilitate the stage of fractionation of the raffinate without increasing the complexity of the process and without modifying the para-xylene yield.

Another advantage of the process according to the invention is that of being able to be taken advantage of in revamping configurations of a xylene loop. This is because, in this case, the same raffinate column can be reused provided that it is fed with the two raffinates introduced separately, as described in stage B according to the invention.

Definitions & Abbreviations

Throughout the description, the terms or abbreviations below have the following meanings.

It is specified that, throughout this description, the expression "between . . . and . . . " should be understood as including the limits mentioned.

The abbreviation EB denotes ethylbenzene.
The abbreviation PX denotes para-xylene.
The abbreviation OX denotes ortho-xylene.
The abbreviation MX denotes meta-xylene.
The term "xylenes (XYL)" is understood to mean a mixture of at least two isomers chosen from ortho-xylene, meta-xylene and para-xylene.
The abbreviation SMB denotes a simulated moving bed.
The term "C9+ hydrocarbons" is understood to mean hydrocarbons containing at least 9 carbon atoms.
The term "C8+ hydrocarbons" is understood to mean hydrocarbons containing at least 8 carbon atoms.
The term "C8 aromatics", also denoted C8A, denotes aromatic hydrocarbons containing 8 carbon atoms chosen from EB, PX, OX or MX.
The term "raffinate" is understood to mean a C8A mixture depleted in PX and which can contain desorbent, that is to say which exhibits a content by weight of PX of less than 2.0%, preferably of less than 1.5% and in a preferred way of less than 1.0%.
Within the meaning of the present invention, the term "devoid" is understood to mean a content by weight of a given compound, with respect to the total weight of the fraction under consideration, for example of EB, of less than 0.5% by weight, preferably of less than 0.1% and in a preferred way of less than 0.01%.
The term "residual amount" of a given compound is understood to mean an amount, the content by weight of which, with respect to the total weight of the fraction under consideration, is less than 5.0% by weight, preferably between 5.0% and 1.0%, preferably between 4.0% and 1.0%, and in a preferred way between 3.0% and 1.0% by weight.
In the present invention, the terms "raffinates", "effluents", "streams" and "fractions" are employed equivalently.

The term "2-cut distillation column" or "3-cut distillation column" is understood to mean a distillation column which makes it possible to obtain two or three fractions respectively.

BRIEF PRESENTATION OF THE FIGURES

DETAILED DESCRIPTION OF THE INVENTION

Figure 1A:
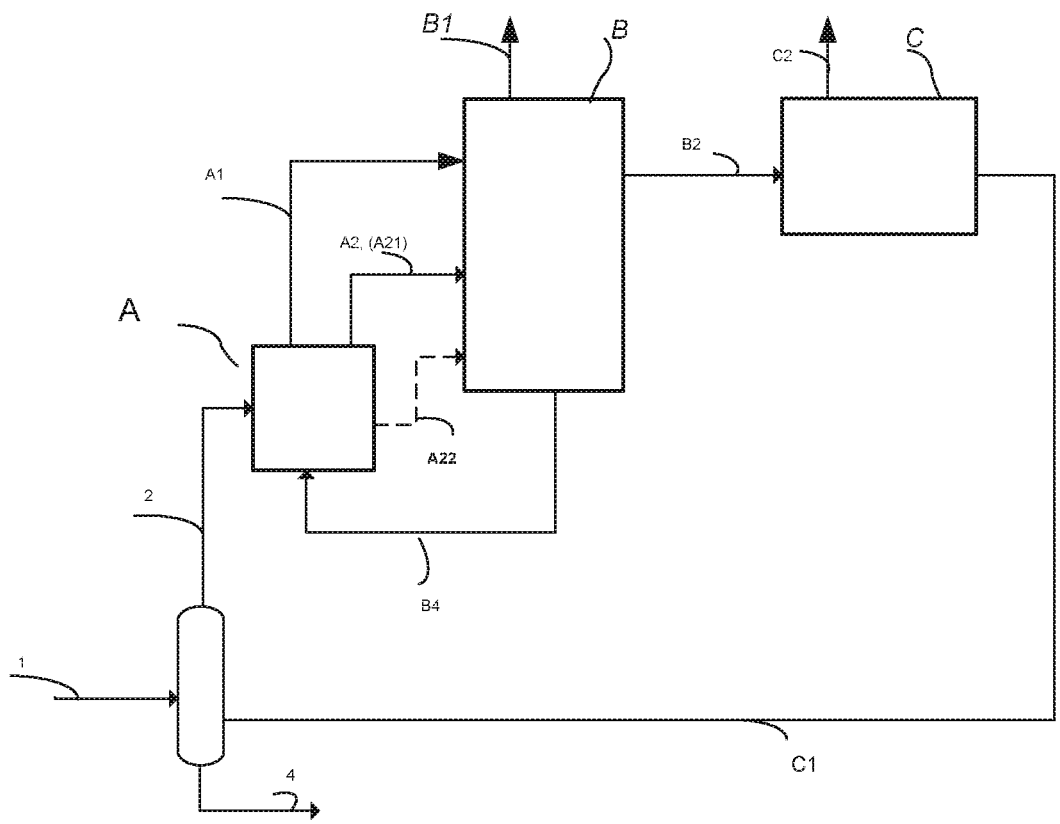
FIG. 1a represents the general scheme of a xylene loop employing a stage of separation by adsorption, a fractionation stage and a vapor-phase isomerization stage C.

The characteristics and advantages of the process according to the invention will become apparent on reading the description below of nonlimiting implementational examples, with reference to the appended figures described below.

Within the meaning of the present invention, the different embodiments presented can be used alone or in combination with one another, without any limit to the combinations.

The present invention relates to a process for obtaining para-xylene from a feedstock containing xylenes, ethylbenzene and C9+ hydrocarbons, said process comprising
  a single stage A of separation in a simulated moving bed of said feedstock, said stage being carried out with a zeolite as adsorbent and a desorbent, at a temperature between 20 and 250° C., under a pressure between the bubble pressure of the xylenes at the operating temperature and 2.0 MPa, and with a ratio by volume of the desorbent to the feedstock in the unit for separation in a simulated moving bed is between 0.4 and 2.5, and making it possible to obtain at least three fractions,
    a fraction A1 comprising a mixture of para-xylene and of desorbent, and
    two fractions A21, A22 comprising ethylbenzene (EB), ortho-xylene (OX) and meta-xylene (MX) and desorbent,
  a stage B of fractionation by distillation in a distillation column of the fractions A21 and A22 resulting from stage A, in which said fractions are introduced separately at distinct injection points, and makes it possible to obtain a fraction B2 containing ethylbenzene, ortho-xylene and meta-xylene, and a fraction B42 devoid of aromatic compounds containing 8 carbon atoms and containing desorbent.

One advantage of the process according to the invention is that of carrying out a prefractionation during the stage of separation in a SMB, which advantageously makes it possible to facilitate the stage of fractionation of the raffinate without increasing the complexity of the process and without modifying the para-xylene yield.

Another advantage of the process according to the invention is that of being able to be taken advantage of in revamping configurations of a xylene loop. This is because, in this case, the same raffinate column can be reused provided that it is fed with the two raffinates introduced separately, as described in stage B according to the invention.

Stage a of Separation in a Simulated Moving Bed

According to the invention, the process (FIG. 2) comprises a single stage A of separation in a simulated moving bed carried out with a zeolite as adsorbent and a desorbent and making it possible to obtain at least three fractions, a fraction A1 containing desorbent and para-xylene two fractions A21 and A22, also called "raffinate", depleted in para-xylene comprising, preferably consisting of, in variable proportions, a mixture of EB, MX, OX, and desorbent.

Advantageously, the proportions of EB, MX, OX and desorbent in the fractions A21 and A22 are different. Preferably, the fraction A21 exhibits a content by weight of desorbent which is lower than that of the fraction A22.

The stage of separation of said feedstock is carried out in a unit operating in a simulated moving bed in at least one separation column containing a plurality of interconnected beds and circulating desorbent in a closed loop, from which the three fractions result:
  the first is an extract A1 comprising para-xylene and desorbent so that, after fractionation to remove the desorbent, the PX reaches a commercial purity of 99.0% minimum and preferentially 99.9% by weight. Advantageously, the extract A1 exhibits at least 30% by weight of the total weight of the extract.
  the PX-depleted fraction A21 comprises, preferably consists of, a mixture of EB, MX, OX, and desorbent.
  the PX-depleted fraction A22 and a residual amount of EB and contains a mixture MX, OX, and desorbent.

Preferably, the adsorbent used in the unit for separation in a simulated moving bed is a barium-exchanged zeolite X or a potassium-exchanged zeolite Y or a barium- and potassium-exchanged zeolite Y.

Preferably, the desorbent used in the unit for separation in a simulated moving bed is chosen from para-diethylbenzene, toluene, para-difluorobenzene or diethylbenzenes, alone or as a mixture.

Preferably, the ratio by volume of the desorbent to the feedstock in the unit for separation in a simulated moving bed is between 0.4 and 2.5, preferably between 0.5 and 2.0 and in a preferred way between 0.5 and 1.5.

Preferably, stage A of separation in a simulated moving bed is carried out at a temperature between 90 and 210° C., and more preferably between 160 and 200° C., and under a pressure between 1.0 and 2.2 MPa and preferably between 1.2 and 2.0 MPa.

Preferably, the adsorber contains a plurality of beds, which are interconnected and spread over several zones delimited by the injections of the feedstock and of the desorbent, and also withdrawals of the extract, and raffinates.

According to a particular embodiment, the total number of beds of the separation unit (SMB) is between 10 and 30 beds, and in a preferred way between 15 and 18 beds, spread over one or more adsorbers, the number of beds being adjusted so that each bed has a height between 0.70 and 1.40 m.

According to a particular embodiment, the distribution of the amount of adsorbent solid in each zone of the separation unit (SMB) is as follows:
  the amount of adsorbent solid in zone 1 is 18%±8%,
  the amount of adsorbent solid in zone 2 is 41%±8%,
  the amount of adsorbent solid in zone 3A is 18%±8%,
  the amount of adsorbent solid in zone 3B is 14%±8%,
  the amount of adsorbent solid in zone 4 is 9%±8%.

Each zone delimits the points of injection and of withdrawal, of the feedstock, desorbent, extract and raffinates as defined below:
  Zone 1 is between the injection of the desorbent B4 and the withdrawal of the extract A1, Zone 2 is between the withdrawal of the extract A1 and the injection of the feedstock, Zone 3A is between the injection of the feedstock and the withdrawal of the raffinate A21, Zone 3B is between the withdrawal of the raffinate A21 and the withdrawal of the raffinate A22, Zone 4 is between the withdrawal of the raffinate A22 and the injection of the desorbent B4.

Advantageously, the performance qualities of stage A of adsorption of the C8A cut devoid of C9+ are characterized by:

the recovery rate of PX in the extract A1, defined by the ratio of PX in the extract A1/PX in the feedstock, is at least equal to 97.0% and that, after recovery of the desorbent, in the extraction column BC-1, the minimum purity of the PX is 99.0% and preferentially greater than 99.9%.

The distribution of the C8As between the two raffinates A21, A22, defined by:

R(C8A)=the amount of C8A in the raffinate A21/the amount of C8A in the total raffinate A2 is at least 60% and preferentially greater than 75%

The distribution of the desorbent between the two raffinates A21, A22, defined by:

R(Desorbent)=the amount of desorbent in the raffinate A21/the amount of desorbent in the total raffinate A2 the separation parameter "delta R", defined by the distribution difference R(C8A)–R(Desorbent).

Preferably, the minimum separation parameter is 10%, preferentially 20% and more preferentially 30%.

Thus, the stage of adsorption A of the feedstock makes it possible to separate the PX, and also to prefractionate the raffinate A2 into two streams, one, A21, enriched in C8A and the other, A22, enriched in desorbent.

Fractionation Stage B

The process according to the invention comprises a stage B of fractionation by distillation in a column of the fractions A21 and A22 resulting from the separation stage A.

According to the invention, said fractions A21 and A22 are introduced separately into the raffinate column B-C2 at distinct injection points.

In a particular embodiment of the invention where the desorbent used in stage A is heavy, that is to say with a greater boiling point than that of the C8As, the fraction having the highest content of heavy desorbent is introduced a few plates below the position of the feeding of the fraction having the lowest content of heavy desorbent.

Advantageously, stage B makes it possible to produce, at the column top, a fraction B2 devoid of desorbent and depleted in PX and containing MX, OX and ethylbenzene and, at the bottom, a fraction B42 devoid of C8A and consisting of desorbent.

One advantage of this double feeding is that of making it possible to reduce the thermal load of the raffinate column by a minimum of 2.0% to 15.0%, depending on the quality of the prefractionation of the raffinates obtained in stage A.

This advantage can be obtained for any type of desorbent insofar as said stage A is implemented so as to carry out a prefractionation into two raffinates A21 and A22, one enriched in desorbent and the other enriched in C8A (OX, MX, EB).

In a particular embodiment of the invention where the desorbent used in stage A is light, that is to say with a lower boiling point than that of the C8As, the fraction of the raffinate having the highest content of light desorbent is introduced a few plates above the position of the feeding of the raffinate having the lowest content of light desorbent.

Advantageously, stage B makes it possible to produce, at the column bottom, a fraction B2 devoid of desorbent and depleted in PX and containing MX, OX and ethylbenzene and, at the top, a fraction B42 devoid of C8A and consisting of desorbent.

Preferably, the distillation column employed is chosen from a 2-cut column and a 3-cut column.

Advantageously, said column exhibits a number of theoretical plates between 30 and 80, preferably between 35 and 75, in a preferred way 40 and 70, very preferably between 45 and 65.

Preferably, the two points for injections of the fractions A21 and A22 into the distillation column exhibits a spacing between 2 and 15 theoretical plates, preferably between 3 and 12 theoretical plates and more preferentially between 4 and 9.

In a preferred embodiment, the distillation column employed is a 2-cut column.

Advantageously, said 2-cut column exhibits a number of theoretical plates between 30 and 70, preferably between 35 and 65, in a preferred way 40 and 60, very preferably between 45 and 55.

Without being bound by any theory, it has been discovered that, to minimize the thermal load of the raffinate column, this spacing is correlated with the quality of the prefractionation of the raffinates carried out in stage A. Preferably, in order to minimize the thermal load of the column B-C2 when the quality of the prefractionation varies, the injection of the fraction A22 will be carried out by a system for distribution on different plates so that the spacing between the points for injection of the feedstocks A21 and A22 increases when the separation parameter R increases. Said 2-cut column additionally comprises a condenser and a reboiler, operated at 0.2 MPa with a reflux ratio of 1.2.

In a particular embodiment, when the desorbent employed in stage A is a heavier compound than the xylenes, that is to say exhibiting a higher boiling point than that of the xylenes, the raffinate enriched in desorbent, that is to say the fraction A22, is introduced below the raffinate depleted in desorbent, that is to say the fraction A21.

In another embodiment, when the desorbent of said separation stage is a lighter compound than the xylenes, that is to say exhibiting a lower boiling point than that of the xylenes, the raffinate enriched in desorbent, that is to say the fraction A21, is introduced above the raffinate depleted in desorbent, that is to say the fraction A22.

In another embodiment, the distillation column employed is a 3-cut column. Preferably, said column comprises an internal wall placed, preferably, in the rectification zone and makes it possible to collect two fractions B2 and B3 devoid of desorbent and a fraction B42 devoid of C8A and comprising, preferably consisting of, desorbent.

Preferably, the injection of the fractions A21 and A22 is carried out on either side of the internal wall. In other words, advantageously, the positions of the two feedings of the fractions A21 and A22 are located on either side of the internal wall.

Preferably, the fraction A1 resulting from stage A containing, and preferably consisting of, a mixture of PX and of desorbent is involved in a stage of fractionation by distillation in a distillation column (B-C1) making it possible to obtain a fraction B1 devoid of desorbent consisting of PX and a fraction B41 consisting of desorbent. Said distillation is carried out according to the knowledge of a person skilled in the art.

Advantageously, the desorbent fractions B41 and B42 devoid of C8A are recovered at the bottom of each distillation column, when the desorbent is heavy, and at the top, when the desorbent is light. Said fractions are subsequently mixed and returned to stage A of adsorption in a simulated moving bed via the stream B4.

Vapor-Phase Isomerization Stage C

The process additionally comprises a stage C of vapor-phase isomerization of the fraction B2 comprising ethylbenzene, ortho-xylene and meta-xylene resulting from the fractionation stage B.

Advantageously, the vapor-phase isomerization stage C makes possible the isomerization of the xylenes and also of the EB, in a unit operating in the vapor phase, at high temperature and converting the ethylbenzene into xylenes, in order to treat the EB-rich raffinate B2 resulting from stage B.

The vapor-phase isomerization stage makes it possible to convert the EB into xylenes with a degree of conversion per pass of the ethylbenzene generally between 10% and 50%, preferably between 20% and 40%, with a loss of C8 aromatics (C8A) of less than 5.0% by weight, preferably of less than 3.0% by weight and preferentially of less than 1.8% by weight.

Advantageously, said stage C also makes it possible to isomerize the xylenes, so that the para-xylene (PX) has a concentration at thermodynamic equilibrium; defined by $$(Ceff-Cin) \times 100/(Ceq-Cin)$$

in which
Ceff and Cin are the PX concentrations respectively in the C8A cut of the effluent and of the feedstock of the isomerization reactor,
Ceq is the concentration at thermodynamic equilibrium of the PX in the C8A cut at the reaction temperature; of greater than or equal to 90%.

The vapor-phase isomerization stage is carried out at a temperature of greater than 300° C., preferably between 350 and 480° C., a pressure of less than 4.0 MPa, preferably between 0.5 and 2.0 MPa, a space velocity of less than 10.0 $h^{-1}$, preferably between 0.5 and 6.0 $h^{-1}$, a hydrogen to hydrocarbon molar ratio of less than 10.0, preferably between 3.0 and 6.0, and in the presence of a catalyst comprising at least one zeolite exhibiting channels, the opening of which is defined by a ring having 10 or 12 oxygen atoms (10 MR or 12 MR), and at least one metal from Group VIII with a content between 0.1% and 0.3% by weight.

All catalysts capable of isomerizing the hydrocarbons having 8 carbon atoms, which may or may not be zeolite-based, are suitable for the vapor-phase isomerization unit. Preferably, a catalyst containing an acidic zeolite, for example of MFI, MOR, MAZ, FAU and/or EUO structural type, is used. More preferably still, a catalyst containing a zeolite of EUO structural type and at least one metal from Group VIII of the Periodic Table of the Elements is used.

According to a preferred variant of the process, the catalyst used in stage C comprises from 1% to 70% by weight of a zeolite of EUO structural type, preferably EU-1, comprising silicon and at least one element T preferably chosen from aluminum and boron, the Si/T ratio of which is between 5 and 100.

Preferably, the zeolite is at least partly in hydrogen form, and the sodium content is such that the Na/T atomic ratio is less than 0.1.

Preferably, the catalyst comprises between 0.01% and 2% by weight of tin or indium, and sulfur in a proportion of from 0.5 to 2 atoms per atom of metal from Group VIII.

The effluent C1 obtained in stage C, exhibiting concentrations of PX, OX and MX isomer close to the concentrations of thermodynamic equilibrium, are recycled to stage A of adsorption in a simulated moving bed.

In a particular embodiment, when the effluent C1 contains heavy and light compounds formed by undesirable reactions, said effluent is then involved in an optional fractionation stage in order to remove said compounds.

EXAMPLES

The examples below illustrate the invention without limiting the scope thereof.

Example 1

This example shows the advantage of the invention by comparing the performance qualities of the distillation stage B placed between an adsorption stage A and an isomerization stage C, said stages forming part of an aromatic complex producing para-xylene from a reformate.

In this example, 543 t/h of a C8 cut resulting from a xylene column and comprising C8 aromatics (C8A) originating from a reformate, from a transalkylation unit and from one or more isomerization units is considered; its composition is, as % by weight:

| | |
|---|---|
| EB | 4.1% |
| PX | 23.1% |
| MX | 50.3% |
| OX | 22.4% |
| C9+ | 0.1% |

Figure 1B:
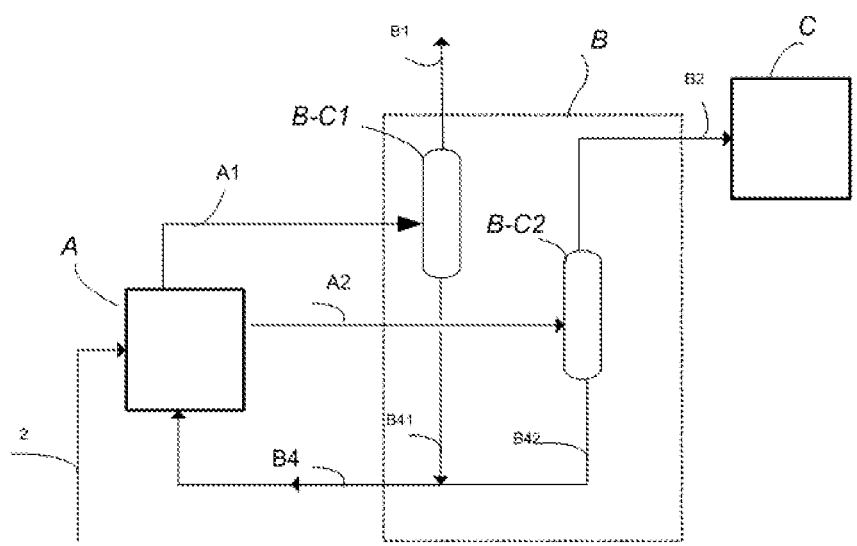
FIG. 1b represents stage B of distillation of the raffinate resulting from stage A according to the prior art.

According to the prior art represented in FIG. 1b), this C8A cut is sent to a stage A of adsorption in a simulated moving bed comprising an adsorber with 4 zones delimited by the injections of feedstocks and of desorbent B4 and the withdrawals of raffinate A2 and of extract A1. This adsorber is composed of 15 beds containing barium-exchanged zeolite X distributed as follows:
   3 beds in zone 1, between the injection of the desorbent B4 and the withdrawal of the extract A1,
   6 beds in zone 2, between the withdrawal of the extract A1 and the injection of the feedstock,
   4 beds in zone 3, between the injection of the feedstock and the withdrawal of the raffinate A2,
   2 beds in zone 4, between the withdrawal of the raffinate A2 and the injection of the desorbent B4.

The temperature is 175° C. The desorbent used is para-diethylbenzene and the solvent content with respect to the feedstock is 1.2 (vol/vol).

Thus employed, the unit for separation by adsorption A makes it possible to produce two streams A1 and A2 feeding the distillation stage B:
   *an extract A1 containing at least 97% of the PX of the feedstock and a portion of the desorbent, which is sent to an extraction column B-C1 in order to recover pure PX at the top (stream B1) and the adsorbent at the bottom (stream B41).
   *827.9 t/h of a raffinate A2 substantially devoid of PX, containing 407.1 t/h of desorbent.

The raffinate A2 is fed to the theoretical plate 25 in the distillation column B-C2 containing 47 theoretical plates, a condenser and a reboiler, operated at 0.2 MPa with a reflux ratio of 1.4. This column makes it possible to produce two streams: 420 t/h of a raffinate at the top B2 containing 25 ppm of desorbent and 407 t/h of desorbent B42 at the bottom containing 50 ppm of xylenes and returned to the simulated moving bed, after mixing with the stream B41 and heat exchange to the temperature required for the adsorption. The fractionation of the raffinate A2 by the raffinate column described thus requires 80 Gcal/h of reboiling energy. The raffinate B2 is sent to the first isomerization stage (C).

Figure 2:
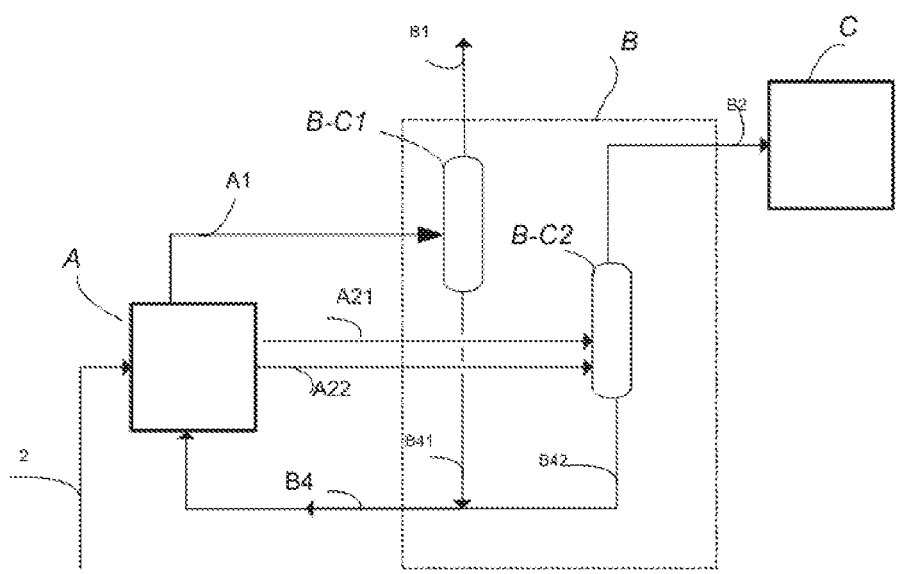
FIG. 2 represents an implementation of the process according to the invention.

In an implementation of the process according to the invention represented in FIG. 2), said C8A cut is sent to a stage A of adsorption in a simulated moving bed comprising an adsorber with 5 zones delimited by the injections of feedstocks and of desorbent (B4) and the withdrawals of the raffinates A21, A22 and of extract A1. Said adsorber is composed of 18 beds containing barium-exchanged zeolite X distributed as follows:

3 beds in zone 1, between the injection of the desorbent B4 and the withdrawal of the extract A1,
6 beds in zone 2, between the withdrawal of the extract A1 and the injection of the feedstock,
4 beds in zone 3A, between the injection of the feedstock and the withdrawal of the raffinate A21,
3 beds in zone 3B, between the withdrawal of the raffinate A21 and the withdrawal of the raffinate A22,
2 beds in zone 4, between the withdrawal of the raffinate A22 and the injection of the desorbent B4.

The temperature is 175° C. The desorbent used is para-diethylbenzene and the solvent content with respect to the feedstock is 1.2 (vol/vol).

Thus, the employment in stage A of the unit for separation by adsorption according to the invention makes it possible to obtain three fractions A1, A21 and A22, according to the following distribution.

an extract A1 containing at least 97% of the para-xylene PX of the feedstock and a portion of the desorbent, which is sent to an extraction column in order to recover pure PX at the top and the desorbent at the bottom,
507.5 t/h of light raffinate A21 and
320.4 t/h of heavy raffinate A22.

The raffinates A21 and A22 are withdrawn from either side of the zone 3B of the unit A for adsorption in a simulated moving bed, and exhibit the following compositions:

R(C8A), the amount of C8A in the raffinate A21/the amount of C8A in the total raffinate=79%
R(Desorbent), the amount of desorbent in the raffinate A21/the amount of desorbent in the total raffinate=43%
The separation parameter Delta R=36%

During stage B of fractionation by the distillation column B-C2 containing 47 theoretical plates, the raffinate A21 is fed to the theoretical plate 24 and the raffinate A22 is fed to the theoretical plate 30. Said column additionally comprises a condenser and a reboiler, operated at 0.2 MPa with a reflux ratio of 1.2. Said column makes it possible to produce the following two fractions:

420 t/h of a raffinate at the top B2 containing MX, OX, EB and 25 ppm of desorbent and
407 t/h of desorbent B42 at the bottom containing 50 ppm of xylenes and returned to the simulated moving bed, after mixing with the stream B41 and heat exchange to the temperature required for the adsorption. The fractionation of the raffinates A21 and A22 by the raffinate column described thus requires 74.4 Gcal/h of reboiling energy. The raffinate B2 is sent to the isomerization stage C.

This example clearly illustrates that obtaining a raffinate enriched in desorbent and a raffinate enriched in MX, OX and EB by the employment in a separation stage A of a unit for adsorption in a simulated moving bed, in combination with their separate introduction into a distillation column, makes it possible to facilitate their fractionation and thus to reduce its thermal load.

Unlike the process described in the prior art where the raffinate column is fed only by a feedstock, it is possible, in accordance with the process according to the invention, to reduce the thermal load of the reboiler by 7%, without adding other stages or other equipment to the aromatic complex known in the prior art.

Example 2

This example illustrates the advantage of the invention, when the performance qualities of the prefractionation of the raffinate during the adsorption stage A vary, as can happen, for example, during a change in setting of the operating parameters of the adsorber or a change in molecular sieve. The conditions of this example are identical to those of example 1. A variation in the separation parameter obtained via a change in sieve is simulated. The position of the feeding of the light raffinate A21 to the raffinate column is not impacted, that of the heavy raffinate is very slightly modified, the heat load saving of the reboiler increases significantly with the quality of the prefractionation of the raffinate.

The improvement in the adsorption capacities and selectivities of the molecular sieve can be made the most of to reduce the energy consumption of the aromatic complex without modifying the configuration of the aromatic complex or its performance qualities in terms of productivity.

|  | Prior art | Case 1 | Case 2 | Case 3 |
| --- | --- | --- | --- | --- |
| R (C8A) | 1 | 0.78 | 0.78 | 0.88 |
| R (Desorbent), | 1 | 0.43 | 0.33 | 0.33 |
| Separation parameter Delta R | 0 | 0.36 | 0.45 | 0.55 |
| Position of the feeding A2 | 25 | NA | NA | NA |
| Position of the feeding A22 | NA | 29 | 30 | 31 |
| Position of the feeding A21 | NA | 24 | 24 | 24 |
| Thermal load of the reboiler (Gcal/h) | 80.0 | 74.4 | 72.6 | 71.0 |
| Energy saying |  | 7% | 9% | 11% |

The invention claimed is:

1. A process for obtaining para-xylene from a feedstock containing xylenes, ethylbenzene and C9+ hydrocarbons, said process comprising
a single stage A in a simulated moving bed of a separation unit (SMB) for separating said feedstock, said stage being carried out with a zeolite as adsorbent and a desorbent, at a temperature between 20 and 250° C., under a pressure between the bubble pressure of the xylenes at the operating temperature and 2.0 MPa, and with a ratio by volume of the desorbent to the feedstock in the stage for separation in a simulated moving bed is between 0.4 and 2.5, and obtaining at least three fractions,
a fraction A1 comprising a mixture of para-xylene and of desorbent, and
two fractions A21, A22, each comprising ethylbenzene (EB), ortho-xylene (OX) and meta-xylene (MX) and desorbent, wherein the proportions of EB, MX, OX and desorbent in the fractions A21 and A22 are different, a stage B of fractionation by distillation in a distillation column of the fractions A21 and A22 resulting from stage A, in which said fractions are introduced separately at distinct injection points, to obtain a fraction B2 containing ethylbenzene, ortho-xylene and meta-xylene, and a fraction B42 devoid of aromatic compounds containing 8 carbon atoms and containing desorbent.

2. The process as claimed in claim 1, in which the distillation column employed in stage B exhibits a number of theoretical plates between 30 and 80.

3. The process as claimed in claim 1, in which the points of injection of the fractions A21 and A22 into the distillation column employed in stage B exhibits a spacing between 2 and 15 theoretical plates.

4. The process as claimed in claim 1, in which the distillation column employed in stage B is chosen from a 2-cut column and a 3-cut column.

5. The process as claimed in claim 1, in which the fraction A21 exhibits a content by weight of desorbent which is lower than that of the fraction A22.

6. The process as claimed in claim 1, in which stage A of separation in a simulated moving bed is carried out at a temperature 90 and 210° C., and under a pressure between 1.0 and 2.2 MPa.

7. The process as claimed in claim 1, in which the total number of beds of the separation unit (SMB) employed in stage A is between 10 and 30 beds.

8. The process as claimed in claim 5, in which the desorbent employed in stage A is a compound exhibiting a higher boiling point than that of the xylenes, and the fraction A22 is introduced below the fraction A21.

9. The process as claimed in claim 5, in which the desorbent employed in stage A is a compound exhibiting a lower boiling point than those of the xylenes, and the fraction A22 is introduced above the A21.

10. The process as claimed in claim 1, further comprising a stage C of vapor-phase isomerization of the fraction B2 comprising ethylbenzene, ortho-xylene and meta-xylene resulting from the fractionation stage B.

11. The process as claimed in claim 10, in which the isomerization stage is carried out at a temperature of greater than 300° C., a pressure of less than 4.0 MPa a space velocity of less than 10.0 $h^{-1}$, a hydrogen to hydrocarbon molar ratio of less than 10.0, and in the presence of a catalyst comprising at least one zeolite exhibiting channels, the opening of which is defined by a ring having 10 or 12 oxygen atoms (10 MR or 12 MR), and at least one metal from Group VIII with a content between 0.1% and 0.3% by weight.

12. The process as claimed in claim 1, in which the distillation column employed in stage B exhibits a number of theoretical plates between 35 and 75.

13. The process as claimed in claim 1, in which the distillation column employed in stage B exhibits a number of theoretical plates between 40 and 70.

14. The process as claimed in claim 1, in which the distillation column employed in stage B exhibits a number of theoretical plates between 45 and 65.

15. The process as claimed in claim 1, in which the points of injection of the fractions A21 and A22 into the distillation column employed in stage B exhibits a spacing between 3 and 12 theoretical plates.

16. The process as claimed in claim 1, in which the total number of beds of the separation unit (SMB) employed in stage A is between 15 and 18 beds.

17. The process as claimed in claim 10, in which the isomerization stage is carried out at a temperature between 350 and 480° C., a pressure between 0.5 and 2.0 MPa, a space velocity between 0.5 and 6.0 $h^{-1}$, a hydrogen to hydrocarbon molar ratio between 3.0 and 6.0, and in the presence of a catalyst comprising at least one zeolite exhibiting channels, the opening of which is defined by a ring having 10 or 12 oxygen atoms (10 MR or 12 MR), and at least one metal from Group VIII with a content between 0.1% and 0.3% by weight.

* * * * *